(12) United States Patent
Hsia et al.

(10) Patent No.: US 6,270,774 B1
(45) Date of Patent: Aug. 7, 2001

(54) NUTRITIONAL SUPPLEMENT COMPOSITION AND USE

(75) Inventors: Houn Simon Hsia, Irvine; David Fan, Mission Veijo, both of CA (US)

(73) Assignee: Viva America Marketing, Inc., Costa Mesa, CA (US)

( * ) Notice: Subject to any disclaimer, the term of this patent is extended or adjusted under 35 U.S.C. 154(b) by 0 days.

(21) Appl. No.: 09/390,952

(22) Filed: Sep. 7, 1999

Related U.S. Application Data

(60) Division of application No. 08/997,807, filed on Dec. 24, 1997, now Pat. No. 5,976,548, which is a continuation-in-part of application No. 08/671,755, filed on Jun. 28, 1996, now abandoned, which is a continuation-in-part of application No. 08/336,845, filed on Nov. 8, 1994, now abandoned.

(51) Int. Cl.[7] ............................ A61K 35/78; A61K 33/32; A23L 1/30
(52) U.S. Cl. ..................... 424/195.1; 424/439; 424/639; 424/641; 424/702; 426/72; 426/541; 426/590; 426/648
(58) Field of Search ................... 424/195.1, 439, 424/639, 641, 702; 426/72, 590, 541, 648

(56) References Cited

U.S. PATENT DOCUMENTS

| | | | | |
|---|---|---|---|---|
| 5,290,605 | * | 3/1994 | Shapira | 424/439 |
| 5,536,506 | * | 7/1996 | Majeed et al. | 424/464 |
| 5,571,441 | * | 11/1996 | Andon et al. | 252/1 |
| 5,637,324 | * | 6/1997 | Bland | 424/655 |

* cited by examiner

Primary Examiner—Christopher R. Tate
(74) Attorney, Agent, or Firm—Lyon & Lyon LLP

(57) ABSTRACT

The present invention relates to nutritional supplements to the human diet used to increase levels of high density lipoprotein (HDL) and calcium ions, and decrease levels of free radicals and glucose in human blood plasma. More specifically, the present invention teaches novel nutritional supplements which comprise a novel combination of specific antioxidants, barley grass extract, specific multiple vitamins and minerals, and ginkgo biloba extract, as well as methods of preparing the nutritional supplements.

4 Claims, 3 Drawing Sheets

NUTRITIONAL SUPPLEMENT COMPOSITION AND USE

RELATED APPLICATIONS

The present application is a division of U.S. application Ser. No. 08/997,807, filed Dec. 24, 1997, now U.S. Pat. No. 5,976,548, which is a continuation-in-part of U.S. application Ser. No. 08/671,755, filed Jun. 28, 1996, now abandoned, which is a continuation-in-part of U.S. application Ser. No. 08/336,845, filed Nov. 8, 1994, which is now abandoned.

BACKGROUND OF THE INVENTION

1. Field of the Invention

The present invention relates to nutritional supplements to the human diet, and more specifically to nutritional supplements which contain a combination of naturally occurring substances such as vitamins and minerals, antioxidants, barley grass extract, and ginkgo biloba extract.

2. Background

Diets complete in nutritional substance are important for the human body in order to afford consistent high levels of optimum performance, both in cognitive ability and physical health. Although the exact needs of the human species to develop and maintain peak performance on a daily basis and sustain such performance for the duration of the human life are not completely understood, it is widely recognized that maintaining balanced nutrition coupled with sensible levels of daily exercise are the fundamental bases for optimizing the condition of the human body. It is also widely accepted that the risk of many common ailments from environmental sources or many ailments arising from genetic consequences can be reduced through the daily practice of, in addition to exercise, a complete nutritional regime fortified with certain vitamins, minerals, food and herb concentrates, especially, in the case of certain genetic consequences, during the antenatal period. Increased human longevity is understood to be a potential consequence of these daily practices.

Cardiovascular disease resulting from the buildup of arterial plaque is a leading cause of illness or death. Arterial plaque is precipitous material formed chiefly of oxidized low density lipoprotein (O-LDL). The buildup of plaque in the form of O-LDL in the arteries is understood to be a factor in ischaemic heart disease. Free radical oxidants, many of which come from naturally occurring sources such as sun exposure, metabolism of certain nutrients, and exercise, act to oxidize low density lipoprotein (LDL) into its deleterious form, O-LDL. Free radical "scavengers" such as vitamins A, E, C, and selenium are believed to react with these oxidants so that they are not available to form O-LDL, thus lowering the risk of arterial plaque deposits in blood vessels. In contrast, the presence of high density lipoprotein (HDL) in the body is understood to have beneficial health effects. Specifically, HDL is known to be a more soluble form of lipoprotein; hence its presence does not significantly contribute to the formation of arterial plaque. In addition, it is known that HDL is able to absorb plaque material and may thus directly reduce the amount of arterial plaque.

3. Description of the Background Art

Certain vitamins and minerals, antioxidants, and plant extracts are generally known to have beneficial health effects. For example, several beneficial aspects of antioxidants have been known for many years. Antioxidants are chemicals that react with free radicals, such as hydroxy radicals, to protect certain biological systems. The removal of free radicals from the body has been suggested to increase human longevity—specifically, the presence of antioxidants including superoxide dismutase (SOD), carotenoids, alpha-tocopherol, and uric acid is suggested to have a positive correlation with resistance to spontaneous autoxidation of tissues and oxidative damage to DNA in mammals [Cutler, R., Am. J. Clin. Nutr., 53:373S–9S (1991)]. Antioxidants are also known to limit destruction of healing brain tissue by free radicals as shown by the method for resuscitating the brain using vitamins such as A, E and C or selenium [See, Klatz et al., U.S. Pat. No. 5,149,321 and PCT application PCT/US92/06681].

In addition to their antioxidant activity, vitamins A, C, and E are well known to have other beneficial health effects. For example, vitamin E is known to help maintain proper blood sugar levels. As another example, vitamin C is known to play an integral role in the integrity of connective and structural tissues in the body. Vitamin A is known to play a role in maintaining good vision as well as in growth and development. Hence, an adequate supply of these vitamins is essential in maintaining optimum health. The use of vitamins A, E, C and selenium has been proposed as a means to inhibit or prevent collagen cross-linking in human skin when used in combination with certain active peptides [See, Geoffrey et al., PCT application WO 90/06102].

Barley grass is known to be a rich source of highly metabolizable vitamins and minerals such as vitamins A, B1, B2, B6, and C, potassium, magnesium, and zinc. In addition, barley grass also has a high concentration of the enzyme superoxide dismutase (SOD), which has been shown to have high levels of antioxidant activity. Barley grass is believed to be an important nutrient in the regulation of the digestive process because the micronutrients, enzymes (e.g., SOD), and fiber contained in barley grass are believed to improve intestinal function [D. Walsh et al., British J. Nutr., 70:621–630 (1993)].

Ginkgo biloba has been a staple Chinese herbal ingredient for thousands of years, and is frequently recommended by Chinese herbal practitioners for coughs, asthma and acute allergic inflammations. There are many active organic compounds in ginkgo biloba, including Ginkgolide B which has been shown to be an active constituent of ginkgo biloba and which apparently works by interfering with platelet activating factor (PAF). PAF is known to have several biological functions, including induction of platelet aggregation, neutrophil degranulation and oxygen radical production, and increasing microvascular permeability and bronchoconstriction. It has been shown that by its inhibitory interaction with PAF, Ginkgolide B helps improve cerebral metabolism and protect the brain against hypoxic damage in laboratory animals with cerebral ischaemia [Kleijnen, J. and Knipschild, P., The Lancet, 340:1136–39 (1992)]. In addition, ginkgo biloba extract is licensed in Germany for the treatment of cerebral dysfunction, hearing loss resulting from cervical syndrome, and peripheral arterial circulatory disturbances with intact circulatory reserve (intermittent claudication) [See, Kleijnen, J. and Knipschild, P., cited above]. Other studies indicate the efficacy of using ginkgo biloba extract to improve mental acuity [See, e.g., Nutrition Today, Jul./Aug.:11–18 (1988); Ginkgo Biloba Extract in Perspective, Auckland, New Zealand: ADIS Press Limited:1 ff (1990))].

A healthy balance of vitamins and minerals has been known to be critical to sustain a healthy human body. Many combinations of vitamins and minerals have been taught over the years as food supplements beneficial to human health, and the daily ingestion of fruits and vegetables has long been recognized as critical to a healthy diet.

There remains a need in the art for novel daily food supplements that provide high levels of antioxidant activity, and thereby increase cardiovascular fortitude, maintain proper blood sugar balance, support mental awareness and intellectual performance, reduce the risk of digestive problems, and strengthen connective and structural tissues.

SUMMARY OF THE INVENTION

The compositions of the present invention are novel combinations of selected ingredients that are known to benefit the human organism. More particularly, the nutritional supplements of the present invention provide a novel combination of antioxidants, other vitamins, minerals, barley grass extract and ginkgo biloba extract. This unique combination of nutrients provides for improved nutrition when ingested by humans.

It is therefore an object of the invention to provide novel compositions containing a combination of specific antioxidants, other vitamins, minerals, a barley grass extract and ginkgo biloba extract.

The present invention also teaches the use of these compositions to supplement the human diet. Therefore, it is an object of the invention to provide a novel method of supplementing the human diet using the dietary supplements taught herein.

It is a further object of the present invention to provide a method of preparing the nutritional supplements of the present invention.

It is yet another object of the present invention to provide nutritional supplements to safely reduce the risk of health problems arising from the presence of free radicals and other oxidants in human blood and tissues.

In still another object, the present invention provides for methods to maintain proper glucose levels in blood serum using the novel nutritional supplements of the invention.

Another object of the present invention is to increase levels of minerals such as calcium in human blood serum and tissues using the novel nutritional supplements of the present invention.

Another object of the present invention is to increase levels of vitamins such as vitamins A and E and other nutrients such as beta-carotene in human blood serum and tissues using the novel nutritional supplements of the present invention.

In a further object, the present invention provides methods for reducing the risk of the harmful biological effects of free radicals and other oxidants in the human system.

In still a further object, the present invention provides novel nutritional supplements used to enhance memory.

DETAILED DESCRIPTION OF THE INVENTION

Figure 1:
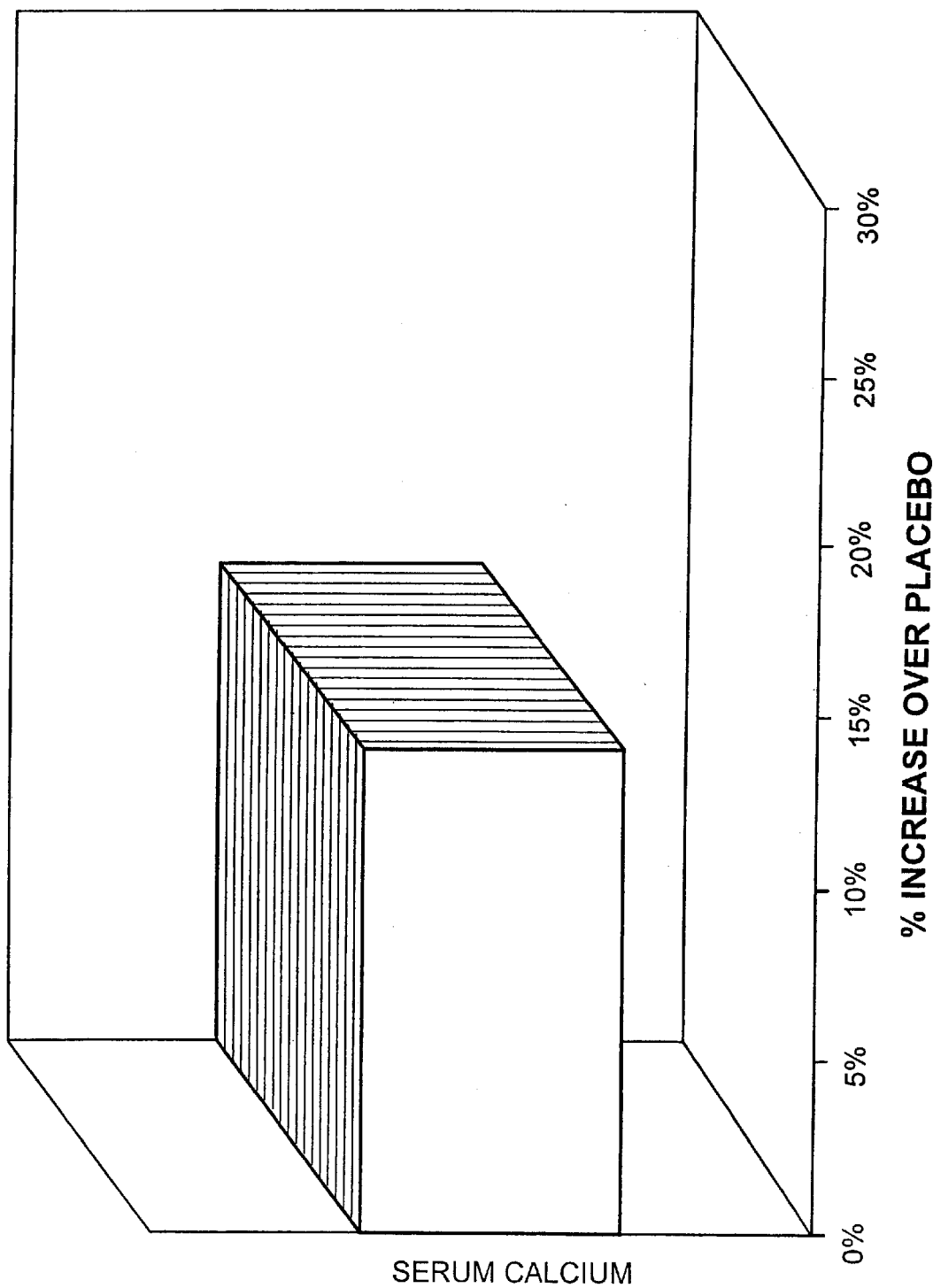
FIG. 1 is a graph illustrating the percentage of increase in serum calcium with multiple vitamins and antioxidants over placebo.

The novel nutritional compositions of the present invention significantly improve the general metabolic, circulatory and nervous systems of the human body, and thus help overcome, or diminish the effect of many of the metabolic problems that occur with the aging of the human system. The present compositions are novel combinations of naturally occurring substances, are non-toxic when administered according to the methods of the present invention, and provide for a more complete nutritional regime.

The present invention focuses on the development and maintenance of vitality and fortitude of the human body as a direct result of the daily oral intake of the compositions of the present invention. The aim of the present invention is to provide compositions that act on the human systems to safely reduce the risks of health problems arising from the presence of oxidants in the human blood and tissues, from elevated glucose levels in blood serum, and from inadequate levels of minerals such as calcium in the human blood serum and tissues. Helping avoid the harmful biological effects of free radicals in the human system, namely inflammation, collagen degradation, and cardiovascular disease, among others, is a prime objective of the present invention. The present invention also provides a composition and method that may maintain proper blood sugar levels and enhance memory.

Some of the observable metabolic changes effected as a direct result of administering the compositions of the present invention are significant, and include: (a) a decrease in blood sugar level; (b) an increase in the concentration of high density lipid protein (HDL) in the blood serum; (c) an increase in blood serum calcium levels, and (d) an increase in blood serum levels of nutrients known to improve human health such as vitamins A and E, and beta-carotene.

Evidence of the effect of the compositions of the invention on calcium ion concentrations and blood glucose levels may be seen in the Examples below. For humans, a normal blood glucose level is approximately 100 mg/dl. It is generally understood that persons. having a blood glucose level of between 100 mg/dl and 150 mg/dl have above-normal levels, and individuals having a blood glucose level of greater than 150 mg/dl are considered diabetic. Since the compositions of the present invention are able to cause an approximate 22% decrease in the level of blood glucose, individuals who have above normal levels of blood glucose may have their levels reduced to normal levels upon administration of the compositions of the present invention.

The compositions of the present invention are also believed to have an effect on memory enhancement because they contain ginkgo, a substance known to have an effect on persons suffering from difficulties of concentration and memory, absent mindedness, confusion, and headaches [See, Kleijnen, J. and Knipschild, P., cited above].

The compositions of the present invention represent a combination of nutritive food supplements that work together with various metabolic systems of the human body. Each novel nutritional supplement composition contains a compendial grade multi-vitamin and mineral dietary supplement; a barley grass extract; a compendial grade of a specified combination of antioxidant vitamins A, C, E, and selenium; and a ginkgo biloba extract. A primary source of the antioxidants and other vitamins and minerals arises from selected food concentrates. These ingredients are combined into nutritional supplements which may be in the form of a solid powder, tablets, lozenges, pills, capsules, or a liquid, and which may be administered alone or in suitable combinations with other components. For example, the nutritional supplement of the present invention may be administered in one or more tablets or lozenges as practical for ease of administration. Each of the vitamins and minerals as well as the ginkgo biloba and barley grass extracts is commercially available, and can be blended to form a single composition or can form multiple compositions which may be co-administered.

DESCRIPTION OF THE PREFERRED EMBODIMENTS

A summary of the ingredients of the food concentrates and their respective antioxidant element(s) is provided in Table I.

TABLE I

| Component | Vitamins and Minerals | Antioxidant Element |
|---|---|---|
| Acorn Squash | Potassium; Calcium, Phosphorus, Vitamin B1, B2, C | Vitamin C |
| Alfalfa | Vitamins A, B1, B2, B6, C, E, K, Niacinamide, Pantothenic acid, Folic acid, Calcium, Copper, Iron, Magnesium, Manganese, Potassium, Phosphorous, Zinc | Vitamins A, C, E |
| Apple | Potassium, Manganese, Cobalt, Molybdenum, Phosphorus, Vanadium, Vitamins A, B1, B2, C, Folic acid | Vitamins A, C |
| Artichoke | Vitamins A, B1, B2, B6, C, Niacinamide, Pantothenic acid, Folic acid, Calcium, Copper, Iron, Magnesium, Manganese, Potassium, Phosphorous, Zinc | Vitamins A, C |
| Avocado | Vitamin A, Calcium, Phosphorus, Iron, Potassium, Sodium, Thiamin, Riboflavin, Niacin, Ascorbic acid | Vitamin A |
| Bananas | Vitamin A, Calcium, Phosphorus, Iron, Potassium, Sodium, Thiamin, Riboflavin, Niacin, Ascorbic acid | Vitamin A |
| Broccoli | Potassium, Magnesium, Calcium, Phosphorus, Vitamins A, E, C, B1 | Vitamins A, C, E |
| Brussels Sprouts | Potassium, Magnesium, Calcium, Copper, Phosphorus, Selenium, Vitamins A, E, C, B2, Folic acid | Vitamins A, E, C, Selenium |
| Cabbage | Vitamins A, B1, B2, C, Niacinamide, Folic acid, Calcium, Iron, Magnesium, Potassium, Phosphorous | Vitamins A, C |
| Cantaloupe | Vitamin A, Calcium, Phosphorus, Iron, Potassium, Sodium, Thiamin, Riboflavin, Niacin, Ascorbic acid | Vitamin A |
| Carrot | Vitamins A, B1, B2, B6, C, Niacinamide, Pantothenic acid, Folic acid, Calcium, Copper, Iron, Magnesium, Manganese, Potassium, Phosphorous, Zinc | Vitamins A, C |
| Cauliflower | Potassium, Magnesium, Calcium, Phosphorus, Vitamins A, E, K, C, Folic acid | Vitamins A, C, E |

TABLE I-continued

| Component | Vitamins and Minerals | Antioxidant Element |
|---|---|---|
| Celery | Potassium, Iron, Calcium, Phosphorus, Vitamins A, E, K, C, Folic acid | Vitamins A, C, E |
| Collard Greens | Potassium, Magnesium, Calcium, Vitamins A, C | Vitamins A, C |
| Grapefruit | Vitamins A and C, Calcium, Phosphorus, Iron, Potassium, Sodium, Thiamin, Riboflavin, Niacin, Ascorbic acid | Vitamins A, C |
| Green Leek | Potassium, Calcium, Copper, Phosphorus, Vitamins E, B2, C | Vitamins E, C |
| Barley grass | Vitamins A, B1, B2, B6, C, K, Niacinamide, Pantothenic acid, Folic acid, Calcium, Copper, Iron, Magnesium, Manganese, Potassium, Phosphorous, Zinc, Superoxide Dismutase (SOD) | Vitamins A, C, SOD |
| Kale | Potassium, Magnesium, Calcium, Chromium, Selenium, Vitamins A, E, C | Vitamins A, C, E, Selenium |
| Kiwi Fruit | Potassium, Magnesium, Calcium, Phosphorus, Vitamins A, C, B1, B2 | Vitamins A, C |
| Lettuce | Potassium, Magnesium, Calcium, Vitamins A, E, C, B1, B2, Folic acid | Vitamins A, C, E |
| Onion | Potassium, Magnesium, Calcium, Copper, Cobalt, Chromium, Vanadium, Phosphorus, Selenium, Vitamins A, B1, B2, C, Biotin, Folic acid | Vitamins A, C, Selenium |
| Papaya | Vitamins A, B1, B2, B6, C, Niacinamide, Pantothenic acid, Calcium, Copper, Iron, Magnesium, Manganese, Potassium, Phosphorous, Zinc | Vitamins A, C |
| Parsley | Vitamins A, B1, B2, B6, C, Niacinamide, Pantothenic acid, Folic acid, Calcium, Copper, Iron, Magnesium, Manganese, Potassium, Phosphorous., Zinc, Para aminobenzoic acid (PABA) | Vitamins, A, C |
| Potato | Potassium, Vitamins A, B2, C, K, E, Folic acid, Phosphorus, Iodide, Calcium, Chromium | Vitamins A, C, and E |
| Prune | Vitamin A, Calcium, Phosphorus, Iron, Potassium, Sodium, Thiamin, Riboflavin, Niacin, Ascorbic acid | Vitamin A |
| Spinach | Vitamins A, B1, B2, B6, C, E, Niacinamide, Pantothenic acid, Folic acid, Calcium, Copper, Iron, Magnesium, Manganese, Potassium, Phosphorous, Zinc | Vitamins A, C, E |
| Strawberry | Vitamins A, B1, B2, B6, C, Niacinamide, Pantothenic acid, Folic acid, Calcium, Copper, Iron, Magnesium, Manganese, Potassium, Phosphorous, Zinc | Vitamins A, C |

TABLE I-continued

| Component | Vitamins and Minerals | Antioxidant Element |
|---|---|---|
| Sweet Potato | Potassium, Vitamins B1, B2, C, Folic acid, Phosphorus, Selenium, Calcium | Vitamin C, Selenium |
| Swiss Chard | Potassium, Magnesium, Calcium, Vitamins A, C | Vitamins A, C |
| Tomato | Potassium, Magnesium, Calcium, Nickel, Chromium, Phosphorus, Boron, Selenium, Vitamins A, C, K, B1, B2, Folic acid | Vitamins A, C, Selenium |

A preferred dosage of the nutritional supplement of the present invention may consist of one or more tablets or lozenges for human oral consumption. If more than one tablet or lozenge is used, each individual tablet or lozenge may be identical to the other tablets or lozenges, or each may contain only some of the ingredients of the nutritional supplement, so that the combination of the different tablets or lozenges comprises the nutritional supplement composition of the present invention.

As a preferred embodiment, a dose of the nutritional supplement composition of the present invention may consist of four tablets or lozenges for human oral consumption. In such an embodiment, the preferred weight of each of the tablets or lozenges is between about 500 mg and about 1,500 mg, and is preferably about 1,000 mg. The total weight of one dose of the nutritional supplement of the present invention is between about 2,000 mg and about 6,000 mg, and most preferably is about 4,000 mg.

The nutritional supplement of the present invention comprises about 5,000 IU to about 20,000 IU of vitamin A, more preferably about 7,500 IU to about 15,000 IU of vitamin A and most preferably about 13,500 IU to about 14,500 IU of vitamin A per dose.

A compendial grade of vitamin C can be employed in the nutritional supplement of the present invention, which comprises, by weight percent, about 200 mg to about 2,000 mg of vitamin C, preferably about 300 mg to about 1,000 mg of vitamin C and most preferably about 450 mg to about 550 mg of vitamin C per dose.

A compendial grade of vitamin E can also be employed in the nutritional supplement of the present composition, which comprises about 100 IU to about 500 IU of vitamin E, preferably about 175 IU to about 425 IU of vitamin E, and most preferably about 175 IU to about 225 IU of vitamin E per dose.

A compendial grade of selenium can be incorporated in the nutritional supplement of the present invention, which comprises, by weight, about 50 micrograms to about 200 micrograms of selenium, preferably about 75 micrograms to about 150 micrograms of selenium, and most preferably about 100 micrograms of selenium per dose.

The total weight of the juice concentrates in the preferred embodiment of the present invention is about 2% to about 20% of the dose of the nutritional supplement of the present invention.

A suitable composition consistent with the present invention comprises juice concentrates having a concentration of at least 10 times that of the native juice in the unconcentrated form, and preferably about 15 times more concentrated, and most preferably about 20 times more concentrated than the unconcentrated juice. In such concentrated form, the juice concentrates are essentially anhydrous, and are generally in powder form.

When present, a form of acorn squash suitable for use to supplement the human diet that can be used in the nutritional supplement of the present invention comprises about 5% to about 25% of the weight of the total juice concentrate composition of the present invention, more preferably about 7.5% to about 15%, and most preferably about 8% to about 12% of the weight of the juice concentrate composition of the present invention.

When present, a form of alfalfa juice suitable for use to supplement the human diet that can be used in the nutritional supplement of the present invention comprises about 2% to about 20% of the weight of the total juice concentrate composition of the present invention, more preferably about 6% to about 12%, and most preferably about 8% to about 10% of the weight of the juice concentrate composition of the present invention.

When present, a form of apple juice suitable for use to supplement the human diet that can be used in the nutritional supplement of the present invention comprises about 2% to about 20% of the weight of the total juice concentrate composition of the present invention, more preferably about 6% to about 12%, and most preferably about 8% to about 10% of the weight of the juice concentrate composition of the present invention.

When present, a form of artichoke juice suitable for use to supplement the human diet that can be used in the nutritional supplement of the present invention comprises about 0.5% to about 10% of the weight of the total juice concentrate composition of the present invention, and preferably about 6% of the weight of the juice concentrate composition of the present invention.

When present, a form of avocado juice suitable for use to supplement the human diet that can be used in the nutritional supplement of the present invention comprises about 0.5% to about 10% of the weight of the total juice concentrate composition of the present invention, and preferably about 1% of the weight of the juice concentrate composition of the present invention.

When present, a form of banana juice suitable for use to supplement the human diet that can be used in the nutritional supplement of the present invention comprises about 0.5% to about 10% of the weight of the total juice concentrate composition of the present invention, and preferably about 1% of the weight of the juice concentrate composition of the present invention.

When present, a form of bell pepper juice suitable for use to supplement the human diet that can be used in the nutritional supplement of the present invention comprises about 0.5% to about 10% of the weight of the total juice concentrate composition of the present invention, and preferably about 1% to about 2% of the weight of the juice concentrate composition of the present invention.

When present, a form of broccoli juice suitable for use to supplement the human diet that can be used in the nutritional supplement of the present invention comprises about 2% to about 20% of the weight of the total juice concentrate composition of the present invention, more preferably about 6% to about 12%, and most preferably about 8.5 to about 10% of the weight of the juice concentrate composition of the present invention.

When present, a form of brussels sprout juice suitable for use to supplement the human diet that can be used in the nutritional supplement of the present invention comprises about 0.25% to about 5% of the weight of the total juice concentrate composition of the present invention, more preferably about 0.35% to about 2.0%, and most preferably about 1.0% of the weight of the juice concentrate composition of the present invention.

When present, a form of cabbage juice suitable for use to supplement the human diet that can be used in the nutritional supplement of the present invention comprises about 2% to about 20% of the weight of the total juice concentrate composition of the present invention, more preferably from about 6% to about 12%, and most preferably about 8% to about 9% of the weight of the juice concentrate composition of the present invention.

When present, a form of cantaloupe juice suitable for use to supplement the human diet that can be used in the nutritional supplement of the present invention comprises about 5% to about 25% of the weight of the total juice concentrate composition of the present invention, more preferably about 7.5% to about 15%, and most preferably about 8% to about 12% of the weight of the juice concentrate composition of the present invention.

When present, a form of carrot juice suitable for use to supplement the human diet that can be used in the nutritional supplement of the present invention comprises about 1% to about 10% of the weight of the total juice concentrate composition of the present invention, more preferably about 2% to about 5.5%, and most preferably about 4.5% to about 5.5% of the weight of the juice concentrate composition of the present invention.

When present, a form of cauliflower juice suitable for use to supplement the human diet that can be used in the nutritional supplement of the present invention comprises about 5% to about 25% of the weight of the total juice concentrate composition of the present invention, more preferably about 7.5% to about 15%, and most preferably about 9% to about 10% of the weight of the juice concentrate composition of the present invention.

When present, a form of celery juice suitable for use to supplement the human diet that can be used in the nutritional supplement of the present invention comprises about 0.5% to about 5% of the weight of the total juice concentrate composition of the present invention, more preferably about 0.6% to about 3%, and most preferably about 0.65% to about 2% of the weight of the juice concentrate composition of the present invention.

When present, a form of collard greens juice suitable for use to supplement the human diet that can be used in the nutritional supplement of the present invention comprises about 1% to about 10% of the weight of the total juice concentrate composition of the present invention, and preferably about 2% of the weight of the juice concentrate composition of the present invention.

When present, a form of grapefruit juice suitable for use to supplement the human diet that can be used in the nutritional supplement of the present invention comprises about 0.5% to about 10% of the weight of the total juice concentrate composition of the present invention, and preferably about 4.0% to about 5.0% of the weight of the juice concentrate composition of the present invention.

When present, a form of green leek juice suitable for use to supplement the human diet that can be used in the nutritional supplement of the present invention comprises about 0.5% to about 10% of the weight of the total juice concentrate composition of the present invention, and preferably about 2% of the weight of the juice concentrate composition of the present invention.

When present, a form of kale juice suitable for use to supplement the human diet that can be used in the nutritional supplement of the present invention comprises about 0.5% to about 5% of the weight of the total juice concentrate composition of the present invention, and preferably about 1% to about 2% of the weight of the juice concentrate composition of the present invention.

When present, a form of kiwi fruit juice suitable for use to supplement the human diet that can be used in the nutritional supplement of the present invention comprises about 0.5% to about 10% of the weight of the total juice concentrate composition of the present invention, and preferably about 1% of the weight of the juice concentrate composition of the present invention.

When present, a form of lettuce juice suitable for use to supplement the human diet that can be used in the nutritional supplement of the present invention comprises about 0.5% to about 10% of the weight of the total juice concentrate composition of the present invention, and preferably about 1% to about 2% of the weight of the juice concentrate composition of the present invention.

When present, a form of onion juice suitable for use to supplement the human diet that can be used in the nutritional supplement of the present invention comprises about 0.5% to about 10% of the weight of the total juice concentrate composition of the present invention, and preferably about 5% of the weight of the juice concentrate composition of the present invention.

When present, a form of orange juice suitable for use to supplement the human diet that can be used in the nutritional supplement of the present invention comprises about 2% to about 20% of the weight of the total juice concentrate composition of the present invention, more preferably about 5% to about 12%, and most preferably about 8% to about 9% of the weight of the juice concentrate composition of the present invention.

When present, a form of papaya juice suitable for use to supplement the human diet that can be used in the nutritional supplement of the present invention comprises about 1% to about 10% of the weight of the total juice concentrate composition of the present invention, more preferably about 1.5% to about 5%, and most preferably about 2% to about 3% of the weight of the juice concentrate composition of the present invention.

When present, a form of parsley juice suitable for use to supplement the human diet that can be used in the nutritional supplement of the present invention comprises about 0.5% to about 8% of the weight of the total juice concentrate composition of the present invention, more preferably about 2% to about 7%, and most preferably about 3% to about 7% of the weight of the juice concentrate composition of the present invention.

When present, a form of potato juice suitable for use to supplement the human diet that can be used in the nutritional supplement of the present invention comprises about 5% to about 25% of the weight of the total juice concentrate composition of the present invention, more preferably about 7.5% to about 15%, and most preferably about 8% to about 12% of the weight of the juice concentrate composition of the present invention.

When present, a form of prune juice suitable for use to supplement the human diet that can be used in the nutritional supplement of the present invention comprises about 5% to about 25% of the weight of the total juice concentrate composition of the present invention, more preferably about 7.5% to about 15%, and most preferably about 8% to about 12% of the weight of the juice concentrate composition of the present invention.

When present, a form of spinach juice suitable for use to supplement the human diet that can be used in the nutritional supplement of the present invention comprises about 0.5% to about 10% of the weight of the total juice concentrate composition of the present invention, more preferably about 1% to about 8%, and most preferably about 6.5% of the weight of the juice concentrate composition of the present invention.

When present, a form of strawberry juice suitable for use to supplement the human diet that can be used in the nutritional supplement of the present invention comprises about 0.5% to about 7.5% of the weight of the total juice concentrate composition of the present invention, and preferably about 2% of the weight of the juice concentrate composition of the present invention.

When present, a form of sweet potato juice suitable for use to supplement the human diet that can be used in the nutritional supplement of the present invention comprises about 0.5% to about 10% of the weight of the total juice concentrate composition of the present invention, and preferably about 2% of the weight of the juice concentrate composition of the present invention.

When present, a form of swiss chard juice suitable for use to supplement the human diet that can be used in the nutritional supplement of the present invention comprises about 0.5% to about 7.5% of the weight of the total juice concentrate composition of the present invention, and preferably about 2% of the weight of the juice concentrate composition of the present invention.

When present, a form of tomato juice suitable for use to supplement the human diet that can be used in the nutritional supplement of the present invention comprises about 1% to about 10% of the weight of the total juice concentrate composition of the present invention, and preferably about 8% of the weight of the juice concentrate composition of the present invention.

The total weight of the combination of non-juice concentrate-derived vitamins and minerals in the nutritional supplements of the present invention is about 10% to about 98% of the total weight of the dose of the nutritional supplement of the present invention, preferably about 15% to about 95% of the weight of the total dose and most preferably about 65% of the weight of the total dose of said nutritional supplement.

In a preferred embodiment, the nutritional supplement of the present invention comprises about 10 IU to about 1,000 IU of vitamin D, more preferably about 15 IU to about 350 IU and most preferably about 275 IU of vitamin D per dose.

In a preferred embodiment, a compendial grade of folic acid or folic acid salt may be employed in the nutritional supplement of the present invention, which comprises, by weight, about 0.03 mg to about 1 mg of folic acid, preferably about 0.1 mg to about 0.5 mg of folic acid, and most preferably about 0.25 mg of folic acid per dose.

In a preferred embodiment, a compendial grade of thiamin (B-1) may be employed in the nutritional supplement of the present invention, which comprises, by weight, about 0.01 mg to about 2.8 mg of thiamin (B-1), preferably about 0.15 mg to about 2.75 mg of thiamin (B-1) and most preferably about 1.75 mg of thiamin (B-1) per dose.

In a preferred embodiment, a compendial grade of riboflavin may be employed in the nutritional supplement of the present invention, which comprises, by weight, about 0.01 mg to about 5.0 mg of riboflavin, preferably about 0.15 mg to about 3.75 mg of riboflavin and most preferably about 3.3 mg of riboflavin per dose.

In a preferred embodiment, a compendial grade of niacin may be employed in the nutritional supplement of the present invention, which comprises, by weight, about 1.0 mg to about 100 mg of niacin, preferably about 5.0 mg to about 20 mg of niacin and most preferably about 15 mg of niacin per dose.

In a preferred embodiment, a compendial grade of vitamin B-6 may be employed in the nutritional supplement of the present invention, which comprises, by weight, about 1.0 mg to about 20.0 mg of vitamin B-6, preferably about 1.5 mg to about 10.5 mg of vitamin B-6 and most preferably about 7 mg of vitamin B-6 per dose.

In a preferred embodiment, a compendial grade of vitamin B-12 may be employed in the nutritional supplement of the present invention, which comprises, by weight, about 1.0 mg to about 20.0 mg of vitamin B-12, preferably about 1.5 mg to about 10.5 mg of vitamin B-12 and most preferably about 5 mg of vitamin B-12 per dose.

In a preferred embodiment, a compendial grade of biotin may be employed in the nutritional supplement of the present invention, which comprises, by weight, about 0.10 mg to about 1.0 mg of biotin, preferably about 0.10 mg to about 0.95 mg of biotin and most preferably about 0.15 mg of biotin per dose.

In a preferred embodiment, a compendial grade of zinc may be employed in the nutritional supplement of the present invention, which comprises, by weight, about 1.0 mg to about 20.0 mg of zinc, preferably about 1.5 mg to about 12.5 mg of zinc and most preferably about 10.0 mg of zinc per dose.

In a preferred embodiment, a compendial grade of calcium may be employed in the nutritional supplement of the present invention, which comprises, by weight, about 10.0 mg to about 500.0 mg of calcium, preferably about 200 mg to about 400 mg of calcium and most preferably about 225 mg to about 275 mg of calcium per dose.

In a preferred embodiment, a compendial grade of manganese may be employed in the nutritional supplement of the present invention, which comprises, by weight, about 1.0 mg to about 10.0 mg of manganese, preferably about 1.15 mg to about 2.75 mg of manganese and most preferably about 2.5 mg of manganese per dose.

The ginkgo biloba extract of the nutritional supplement of the present invention consists of about 20 mg to about 100 mg, more preferably from about 25 mg to about 50 mg and most preferably from about 26 mg to about 35 mg ginkgo biloba extract [Westar Nutrition, Inc.] per dose.

The siberian ginseng extract of the nutritional supplement of the present invention consists of about 5 mg to about 90 mg, more preferably from about 7 mg to about 75 mg, and most preferably from about 9 mg to about 11 mg siberian ginseng extract per dose.

The barley grass extract of the nutritional supplement of the present invention consists of about 100 mg to about 400 mg, more preferably from about 150 mg to about 300 mg and most preferably from about 190 mg to about 230 mg barley grass extract per dose.

To prepare the components of the invention, each of the active ingredients may be combined in intimate admixture with a suitable carrier according to conventional compounding techniques. This carrier may take a wide variety of forms depending upon the form of preparation desired for administration, e.g., oral, sublingual, nasal, or parenteral. As disclosed above, in the most preferred embodiment, the nutritional supplement comprises four tablets or lozenges, the composition of each being identical to each other tablet or lozenge. Alternatively, some of the ingredients may be combined with a suitable carrier to form one dosage form, such as a tablet or lozenge, and the remaining ingredients may be combined with a suitable carrier to form a second dosage form, such as a second tablet or lozenge. The ingredients may be mixed into as many dosage forms as desired to provide, for example, ease of administration.

In preparing the compositions in oral dosage form, any of the usual media may be employed. For oral liquid preparations (e.g., suspensions, elixirs, and solutions), media containing, for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, tablets, and lozenges). Controlled release forms may also be used. Because of their ease in administration, tablets, pills, and capsules represent the most advantageous oral dosage unit form, in which case solid carriers are obviously employed. If desired, tablets may be sugar coated or enteric coated by standard techniques.

In preparing the compositions of the invention, the above-described active ingredients may be combined with a variety of non-essential ingredients which perform the functions described in the above description of dosage forms. Such non-essential ingredients may include in weight per dose: about 1 mg to about 15 mg pantothenic acid; about 0.01 mg to about 0.1 mg potassium iodide; about 5 mg to about 25 mg iron; about 25 mg to about 150 mg magnesium oxide; about 0.1 mg to about 2.0 mg copper gluconate; about 25 mcg to about 75 mcg molybdenum; about 100 mcg to about 200 mcg chromium; about 5 mcg to about 200 mcg selenium; about 2 mg to about 15 mg choline; and about 2 mg to about 15 mg inositol.

The following examples are illustrative only, and do not purport to limit the invention in any fashion.

EXAMPLE 1

The following composition falls within the preferred embodiment of the present invention, and is in the form of four identical tablets for administration.

| Tablet weight: Approximately 1000 mg Dose = 4 tablets | |
|---|---|
| Ingredient | Approximate Amount Per Dose |
| Vitamin A | 14,100 IU |
| Vitamin D3 | 275 IU |
| Vitamin E | 177 IU |
| Vitamin C | 530 mg |
| Folate | 0.21 mg |
| Thiamin | 1.7 mg |
| Riboflavin | 3.3 mg |
| Niacinamide | 15.5 mg |
| Vitamin B6 | 7 mg |
| Vitamin B12 | 4.8 mcg |
| Biotin | 0.16 mg |
| d-Calcium Pantothenate | 7.5 mg |
| Calcium (Calcium Carbonate) | 185.6 mg |
| Calcium (Di-Calcium Phosphate) | 64 mg |
| Phosphorous | 50 mg |
| Iodine | 0.075 mg |

-continued

| Tablet weight: Approximately 1000 mg Dose = 4 tablets | | |
|---|---|---|
| Ingredient | Approximate Amount Per Dose | |
| Iron | 9 mg | |
| Magnesium | 104.3 mg | |
| Copper | 1 mg | |
| Zinc | 10 mg | |
| Manganese | 2.5 mg | |
| Selenium | 100 mcg | |
| Molybdenum | 50 mcg | |
| Chromium | 100 mcg | |
| Choline | 11.6 mg | |
| Inositol | 14 mg | |
| PABA | 15 mg | |
| Ginkgo Biloba Extract | 30 mg | |
| Siberian Ginseng Extract | 10 mg | |
| Barley Grass Juice Concentrate | 200 mg | |
| Kelp | 10 mg | |
| Magnesium Stearate | 20 mg | |
| Juice concentrates (approximately 113 mg total) | | |
| Alfalfa Juice Powder | 10 | mg |
| Parsley Powder | 7.175 | mg |
| Spinach Powder | 7.175 | mg |
| Carrot Powder | 5.415 | mg |
| Cabbage Powder | 9.741 | mg |
| Apple Powder | 10.107 | mg |
| Artichoke Powder | 7.175 | mg |
| Papaya Powder | 2.707 | mg |
| Tomato Powder | 8.935 | mg |
| Broccoli Powder | 10.871 | mg |
| Kale Powder | 1.760 | mg |
| Celery Powder | 1.760 | mg |
| Orange Powder | 9.831 | mg |
| Brussels Sprout Powder | 1.354 | mg |
| Grapefruit Powder | 5.415 | mg |
| Bell Pepper Powder | 1.354 | mg |
| Lettuce Powder | 1.354 | mg |

EXAMPLE 2

The following composition falls within the preferred embodiment of the present invention, and is in the form of four identical tablets for administration.

| Tablet weight: Approximately 1000 mg Dose = 4 tablets | |
|---|---|
| Ingredient | Approximate Amount Per Dose |
| Vitamin A | 14,350 IU |
| Vitamin D3 | 275 IU |
| Vitamin E | 210 IU |
| Vitamin C | 450 mg |
| Folate | 0.21 mg |
| Thiamin | 1.7 mg |
| Riboflavin | 3.5 mg |
| Niacinamide | 14.75 mg |
| Vitamin B6 | 7 mg |
| Vitamin B12 | 4.8 mcg |
| Biotin | 0.16 mg |
| d-Calcium Pantothenate | 7.5 mg |
| Calcium (Calcium Carbonate) | 185.6 mg |
| Calcium (Di-Calcium Phosphate) | 64 mg |
| Phosphorous | 50 mg |
| Iodine | 0.075 mg |
| Iron | 9 mg |
| Magnesium | 104.3 mg |
| Copper | 1 mg |
| Zinc | 10 mg |
| Manganese | 2.5 mg |

-continued

Tablet weight: Approximately 1000 mg
Dose = 4 tablets

| Ingredient | Approximate Amount Per Dose |
|---|---|
| Selenium | 100 mcg |
| Molybdenum | 50 mcg |
| Chromium | 100 mcg |
| Choline | 11.6 mg |
| Inositol | 14 mg |
| PABA | 15 mg |
| Ginkgo Biloba Extract | 30 mg |
| Siberian Ginseng Extract | 10 mg |
| Barley Grass Juice Concentrate | 200 mg |
| Kelp | 10 mg |
| Magnesium Stearate | 20 mg |
| Juice concentrates (approximately 113 mg total) | |
| Alfalfa Juice Powder | 10 mg |
| Parsley Powder | 7.175 mg |
| Spinach Powder | 7.175 mg |
| Carrot Powder | 5.415 mg |
| Cabbage Powder | 9.741 mg |
| Apple Powder | 10.107 mg |
| Artichoke Powder | 7.175 mg |
| Papaya Powder | 2.707 mg |
| Tomato Powder | 8.935 mg |
| Broccoli Powder | 10.871 mg |
| Kale Powder | 1.760 mg |
| Cauliflower Powder | 10.871 mg |
| Celery Powder | 1.760 mg |
| Orange Powder | 9.831 mg |
| Brussels Sprout Powder | 1.354 mg |
| Grapefruit Powder | 5.415 mg |
| Bell Pepper Powder | 1.354 mg |
| Lettuce Powder | 1.354 mg |

EXAMPLE 3

The following composition falls within the preferred embodiment of the present invention, and is in the form of four identical tablets for administration.

Tablet weight: Approximately 1000 mg
Dose = 4 tablets

| Ingredient | Approximate Amount Per Dose |
|---|---|
| Vitamin A | 14,100 IU |
| Vitamin D3 | 275 IU |
| Vitamin E | 160 IU |
| Vitamin C | 550 mg |
| Folate | 0.225 mg |
| Thiamin | 1.7 mg |
| Riboflavin | 3.5 mg |
| Niacinamide | 14.75 mg |
| Vitamin B6 | 7 mg |
| Vitamin B12 | 4.8 mcg |
| Biotin | 0.16 mg |
| d-Calcium Pantothenate | 7.5 mg |
| Calcium (Calcium Carbonate) | 185.6 mg |
| Calcium (Di-Calcium Phosphate) | 64 mg |
| Phosphorous | 50 mg |
| Iodine | 0.075 mg |
| Iron | 9 mg |
| Magnesium | 104.3 mg |
| Copper | 1 mg |
| Zinc | 10 mg |
| Manganese | 2.5 mg |
| Selenium | 100 mcg |
| Molybdenum | 50 mcg |
| Chromium | 100 mcg |
| Choline | 11.6 mg |

-continued

Tablet weight: Approximately 1000 mg
Dose = 4 tablets

| Ingredient | Approximate Amount Per Dose |
|---|---|
| Inositol | 14 mg |
| PABA | 15 mg |
| Ginkgo Biloba Extract | 30 mg |
| Siberian Ginseng Extract | 10 mg |
| Barley Grass Juice Concentrate | 200 mg |
| Kelp | 10 mg |
| Magnesium Stearate | 20 mg |
| Juice concentrates (approximately 113 mg total) | |
| Alfalfa Juice powder | 10 mg |
| Parsley Powder | 7.175 mg |
| Spinach Powder | 7.175 mg |
| Carrot Powder | 5.415 mg |
| Cabbage Powder | 9.741 mg |
| Apple Powder | 10.107 mg |
| Artichoke Powder | 7.175 mg |
| Papaya Powder | 2.707 mg |
| Tomato Powder | 8.935 mg |
| Broccoli Powder | 10.871 mg |
| Kale Powder | 1.760 mg |
| Cauliflower Powder | 10.871 mg |
| Celery Powder | 1.760 mg |
| Orange Powder | 9.831 mg |
| Brussels Sprout Powder | 1.354 mg |
| Grapefruit Powder | 5.415 mg |
| Bell Pepper Powder | 1.354 mg |
| Lettuce Powder | 1.354 mg |

EXAMPLE 4

A study was undertaken to evaluate the effect of the present invention on serum lipid profile, serum calcium levels, and serum sugar levels. The objectives of the study were to determine (1) whether oral intake of the composition results in increased levels of calcium ion in the human blood; (2) whether oral intake of the composition influences the levels of HDL in the lipid fraction distribution; and (3) whether oral intake of the composition influences the blood glucose levels.

A total of 50 subjects with ages between 45 and 65 years with abnormal lipid profiles were divided into 2 groups. One group (25 subjects) received placebo packages and ingested this twice a day, once in the morning and once in the evening. The other group (25 subjects) received a composition of the present invention, as set forth in Example I, and ingested twice daily, once in the morning and once in the afternoon. The below-described results were compiled after a 2-month testing period. The identity of the tablets was unknown by the subjects, and to the examiner (i.e., a double blind study). Blood serum (approximately 4 cc) was collected at the starting time and again after the completion of two months of usage. A fasting lipid profile was conducted on the plasma samples using a lipid fractionation panel automated system [Hewlett-Packard Co.]. In addition, measurements of electrolytes (including calcium ion) and glucose levels were made using the Chem 18 automated system [Hewlett-Packard Co.].

Figure 2:
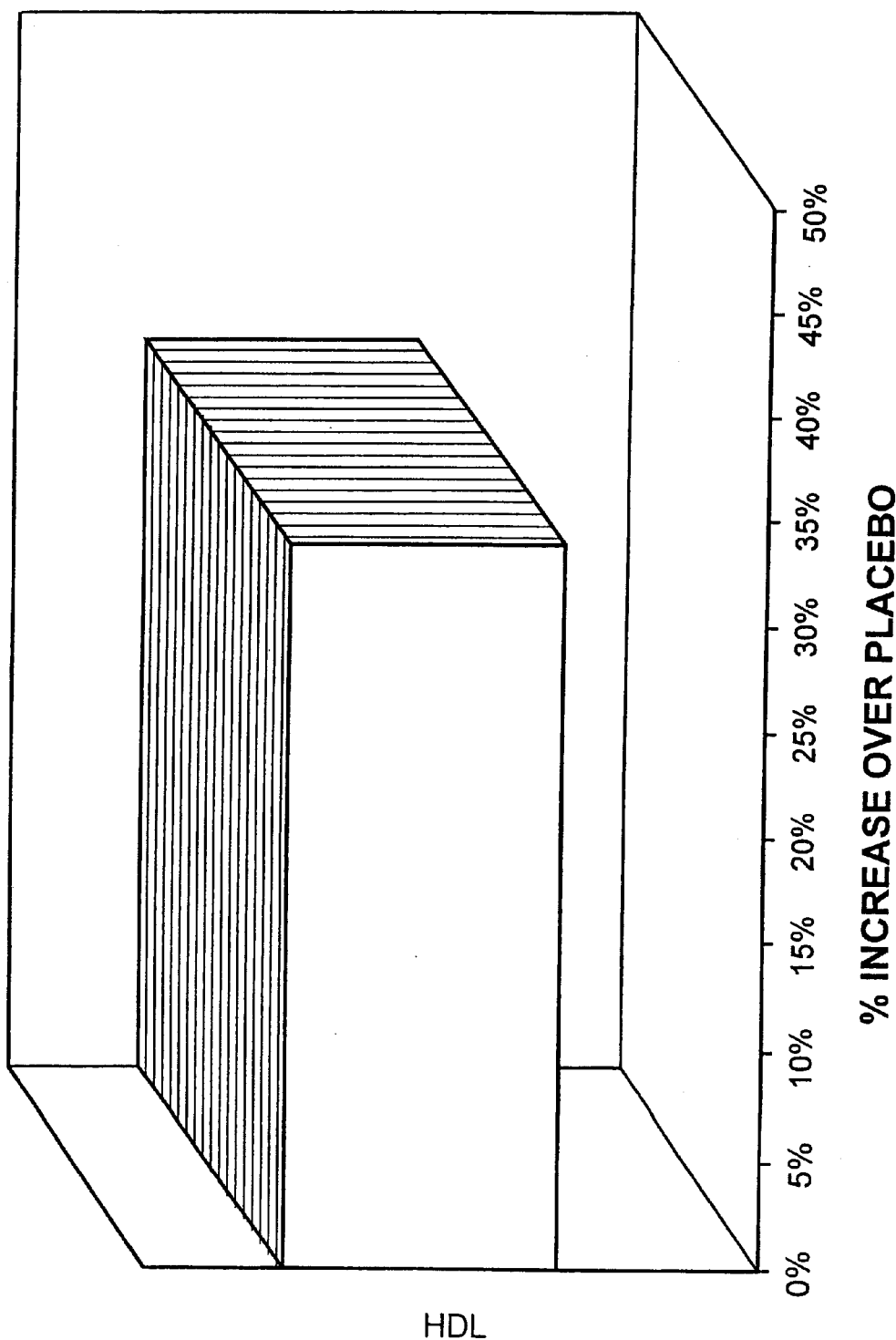
FIG. 2 is a graph illustrating the percentage of increase in HDL with multiple vitamins and antioxidants over placebo.
Figure 3:
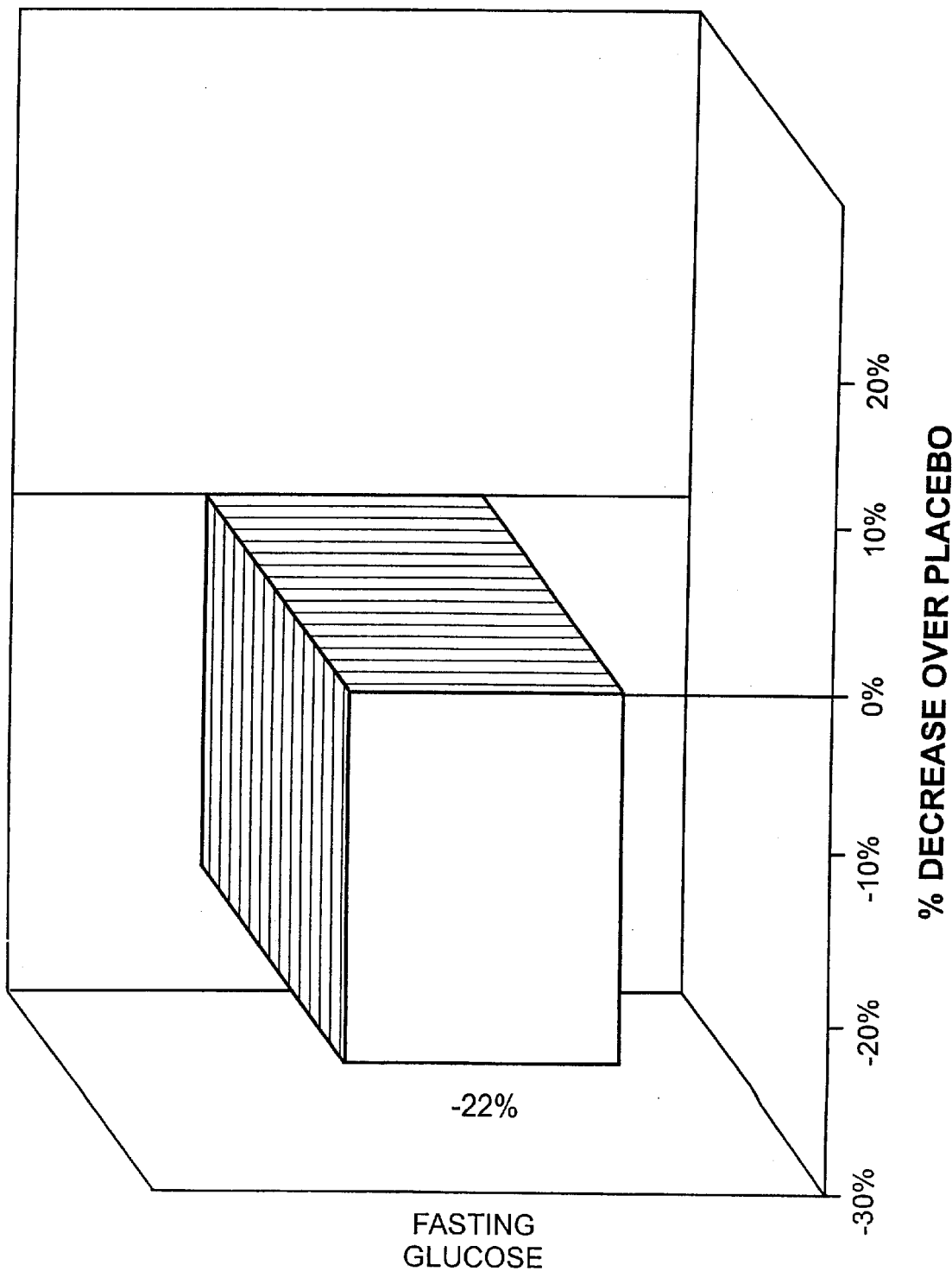
FIG. 3 is a graph illustrating the percentage of increase in fasting glucose with multiple vitamins and antioxidants over placebo.

The results demonstrated (1) a statistically significant increase in the calcium ion levels for subjects using the composition of Example I over those using the placebo (see FIG. 1, showing the percentage increase in calcium over the placebo); (2) a statistically significant increase in the levels of HDL of about 35% was observed for subjects using the composition of Example I over those using the placebo (see FIG. 2, showing the percentage increase in HDL over the placebo); and (3) a statistically significant decrease in the levels of glucose of about 22% was observed for subjects using the composition of Example I over those using the placebo (see FIG. 3, showing the percentage decrease in blood glucose over the placebo).

Numerous modifications and variations of the present invention are included in the above-identified specification and are expected to be obvious to one of skill in the art. It is also intended that the present invention cover modifications and variations of the compositions and methods for using them to accomplish their claimed uses within the scope of the appended claims and their equivalents.

What is claimed is:

1. A method of increasing levels of high density lipoprotein (HDL) in human blood plasma comprising the step of administering daily a nutritional supplement comprising:

a plurality of antioxidants comprising between approximately 5,000 IU and approximately 20,000 IU vitamin A, between approximately 100 IU and approximately 500 IU vitamin E, between approximately 200 mg and approximately 2,000 mg vitamin C, and between approximately 50 mcg and approximately 200 mcg selenium;

between approximately 100 mg and approximately 400 mg of a barley grass extract; between approximately 20 mg and approximately 100 mg of a ginkgo biloba extract; and a juice concentrate comprising between approximately 2% and approximately 20% of the dose of the nutritional supplement, wherein between approximately 2% and approximately 20% of the juice concentrate is alfalfa juice concentrate, between approximately 0.5% and approximately 10% of the juice concentrate is artichoke concentrate, between approximately 2% and approximately 20% of the juice concentrate is broccoli juice concentrate, and between approximately 0.5% and approximately 8% of the juice concentrate is parsley juice concentrate.

2. The method of claim 1, wherein the juice concentrate additionally comprises a plurality of juice concentrates selected from the group consisting of acorn squash, apple, avocado, bananas, bell peppers, brussels sprouts, cabbage, cantaloupe, carrot, cauliflower, celery, collard greens, grapefruit, green leek, kale, kiwi fruit, lettuce, onion, orange, papaya, potato, prune, spinach, strawberry, sweet potato, swiss chard, and tomato.

3. The method of claim 1, wherein the juice concentrate has a concentration of at least 10 times that of native juice in the unconcentrated form.

4. The method of claim 1, wherein the nutritional supplement further comprises one or more vitamins and/or minerals selected from the group consisting of vitamin D, folic acid, thiamin (B-1), riboflavin, niacin, vitamin B-6, vitamin B-12, biotin, zinc, and manganese.

* * * * *